US007449552B2

(12) United States Patent
Abad et al.

(10) Patent No.: US 7,449,552 B2
(45) Date of Patent: Nov. 11, 2008

(54) ***BACILLUS THURINGIENSIS* CRY GENE AND PROTEIN**

(75) Inventors: Andre R. Abad, West Des Moines, IA (US); Ronald D. Flannagan, Grimes, IA (US); Billy F. McCutchen, Cameron, TX (US); Cao Guo Yu, Irvine, CA (US)

(73) Assignees: Pioneer Hi-Bred International, Inc., Johnston, IA (US); E.I. duPont deNemours and Company, Wilmington, DE (US)

( * ) Notice: Subject to any disclaimer, the term of this patent is extended or adjusted under 35 U.S.C. 154(b) by 49 days.

(21) Appl. No.: 11/404,297

(22) Filed: Apr. 14, 2006

(65) Prior Publication Data

US 2007/0245427 A1 Oct. 18, 2007

(51) Int. Cl.
*C07K 14/325* (2006.01)
(52) U.S. Cl. ...................................................... 530/350
(58) Field of Classification Search ....................... None
See application file for complete search history.

(56) References Cited

U.S. PATENT DOCUMENTS

2002/0151709 A1 10/2002 Abad et al.

FOREIGN PATENT DOCUMENTS

EP 498537 A2 * 8/1992
JP 2002045186 A 10/2002

OTHER PUBLICATIONS de Maagd et al, 1999, Appl. Environ. Microbiol. 65:4369-4374.*
Tounsi et al, 2003, J. Appl. Microbiol. 95:23-28.*
Aronson et al, 2001, FEMS Microbiol. Lett. 195:1-8.*
De Maagd et al, 2001, Trends Genet. 17:193-199.*
Guo et al, 2004, Proc. Natl. Acad. Sci. USA 101: 9205-9210.*
Walters et al, 1993, Biochem. Biophys. Res. Comm. 196:921-926.*
Asano, et al., A strain of *Bacillus thuringiensis* subsp. *galleriae* containing a novel cry8 gene highly toxic to *Anomala cuprea* (Coleoptera: Scarabaeidae), Biol. Control, (2003), 28: 191-196.
Sato, et al., Cloning, Heterologous Expression, and Localization of a Novel Crystal Protein Gene from *Bacillus thuringiensis serovar japonensis* Strain Buibui Toxic to Scarabaeid Insects, Current Microbiol., (1994), 28:15-19.

* cited by examiner

*Primary Examiner*—Anne R Kubelik

(57) ABSTRACT

Compositions and methods for protecting a plant from an insect pest are provided. In particular, novel polynucleotides and the pesticidal polypeptides they encode are provided. Methods of using the novel polynucleotides and pesticidal polypeptides of the invention to protect a plant from an insect pest are further provided. Particular embodiments of the invention provide pesticidal compositions and formulations, DNA constructs, and transformed plants, plant cells, and seeds.

1 Claim, No Drawings

SEQUENCE LISTING

```
<160> NUMBER OF SEQ ID NOS: 4

<210> SEQ ID NO 1
<211> LENGTH: 2166
<212> TYPE: DNA
<213> ORGANISM: Bacillus thuringiensis
<220> FEATURE:
<221> NAME/KEY: CDS
<222> LOCATION: (1)...(2160)

<400> SEQUENCE: 1 atg agt cca aat aat caa aat gaa tat gaa att ata gat gcg aca cct        48
Met Ser Pro Asn Asn Gln Asn Glu Tyr Glu Ile Ile Asp Ala Thr Pro
1               5                   10                  15 tct act tct gta tcc aat gat tct aac

-continued

| | | |
|---|---|---|
| gaa ctg gat ttt gtt gga gca att cca tcc ttt gca gta tcc ggg cag<br>Glu Leu Asp Phe Val Gly Ala Ile Pro Ser Phe Ala Val Ser Gly Gln<br>180 185 190 | | 576 |
| gaa gta cca tta tta gca gta tat gca cag gct gtg aac atg cac tta<br>Glu Val Pro Leu Leu Ala Val Tyr Ala Gln Ala Val Asn Met His Leu<br>195 200 205 | | 624 |
| ttg tta cta aga gac gct tct att ttt gga gaa gag tgg gga ttc aca<br>Leu Leu Leu Arg Asp Ala Ser Ile Phe Gly Glu Glu Trp Gly Phe Thr<br>210 215 220 | | 672 |
| tca tct gaa att tcc act tac tac aac cgt caa gtg caa ctc act tct<br>Ser Ser Glu Ile Ser Thr Tyr Tyr Asn Arg Gln Val Gln Leu Thr Ser<br>225 230 235 240 | | 720 |
| caa tat tcc gat tat tgt gtg aag tgg tac gat acc ggt tta cag aaa<br>Gln Tyr Ser Asp Tyr Cys Val Lys Trp Tyr Asp Thr Gly Leu Gln Lys<br>245 250 255 | | 768 |
| tta aaa ggt acg agc gct gag agt tgg ctg gag tat cat caa ttc cgc<br>Leu Lys Gly Thr Ser Ala Glu Ser Trp Leu Glu Tyr His Gln Phe Arg<br>260 265 270 | | 816 |
| aga gag atg act ttc atg gta tta gat ttg gtt gca tta ttt cca aac<br>Arg Glu Met Thr Phe Met Val Leu Asp Leu Val Ala Leu Phe Pro Asn<br>275 280 285 | | 864 |
| tac gat aca cac acg tat cca ctt gaa aca aag gct caa ctt aca cga<br>Tyr Asp Thr His Thr Tyr Pro Leu Glu Thr Lys Ala Gln Leu Thr Arg<br>290 295 300 | | 912 |
| gaa gta tat acg gat ccg atc gcc ttt aat ctt tct ggg gca gcg ggt<br>Glu Val Tyr Thr Asp Pro Ile Ala Phe Asn Leu Ser Gly Ala Ala Gly<br>305 310 315 320 | | 960 |
| ttt tgt agc cct tgg tca aag tat act ggt att tcc ttt tcg gag att<br>Phe Cys Ser Pro Trp Ser Lys Tyr Thr Gly Ile Ser Phe Ser Glu Ile<br>325 330 335 | | 1008 |
| gaa aat gat gta att cgt ccg cct cat tta ttt aat cta ctc aga agt<br>Glu Asn Asp Val Ile Arg Pro Pro His Leu Phe Asn Leu Leu Arg Ser<br>340 345 350 | | 1056 |
| tta gag att aat aca gtt agg ggg aca att tta ggt aat act aaa gat<br>Leu Glu Ile Asn Thr Val Arg Gly Thr Ile Leu Gly Asn Thr Lys Asp<br>355 360 365 | | 1104 |
| tac cta aac tat tgg tca ggt cat tct cta caa tat aat ttt ata ggt<br>Tyr Leu Asn Tyr Trp Ser Gly His Ser Leu Gln Tyr Asn Phe Ile Gly<br>370 375 380 | | 1152 |
| aag aca ata gtc agg gaa agt aat tat gga tat ctt act tca gaa aaa<br>Lys Thr Ile Val Arg Glu Ser Asn Tyr Gly Tyr Leu Thr Ser Glu Lys<br>385 390 395 400 | | 1200 |
| act agg att gaa tta gac act aga gat att ttt gaa att aat tca act<br>Thr Arg Ile Glu Leu Asp Thr Arg Asp Ile Phe Glu Ile Asn Ser Thr<br>405 410 415 | | 1248 |
| gcc gca agc tta gcg aat tac tat caa gag act tat ggt gtg cca gaa<br>Ala Ala Ser Leu Ala Asn Tyr Tyr Gln Glu Thr Tyr Gly Val Pro Glu<br>420 425 430 | | 1296 |
| tct agg ctc cat ttg gtg aga tgg gct agc cca tat tat aca tca tct<br>Ser Arg Leu His Leu Val Arg Trp Ala Ser Pro Tyr Tyr Thr Ser Ser<br>435 440 445 | | 1344 |
| cat ctt tat tct aaa aca cat aca act gga gaa ggt tgt aca caa gtt<br>His Leu Tyr Ser Lys Thr His Thr Thr Gly Glu Gly Cys Thr Gln Val<br>450 455 460 | | 1392 |
| tat gaa tca agt gag gaa ata cct gta gac aga acc gta ccg ata aat<br>Tyr Glu Ser Ser Glu Glu Ile Pro Val Asp Arg Thr Val Pro Ile Asn<br>465 470 475 480 | | 1440 |
| gaa ggt tat agt cac aga cta tcg tat gtc acc gct ctc ttt ttc cag<br>Glu Gly Tyr Ser His Arg Leu Ser Tyr Val Thr Ala Leu Phe Phe Gln | | 1488 |

```
                    485                 490                 495
aaa att att aat act ttt tat aga aat gga act cta cct gtc ttt gtt    1536
Lys Ile Ile Asn Thr Phe Tyr Arg Asn Gly Thr Leu Pro Val Phe Val
            500                 505                 510 tgg aca cat cga agt gca gat ctt aca aat aca att tat cca gat gta    1584
Trp Thr His Arg Ser Ala Asp Leu Thr Asn Thr Ile Tyr Pro Asp Val
        515                 520                 525 att act caa ata cca gtg gta aag gcc tat gaa ttg ggt agc tcc atc    1632
Ile Thr Gln Ile Pro Val Val Lys Ala Tyr Glu Leu Gly Ser Ser Ile
    530                 535                 540 tta cca gat agt cca tca cct act att gtg cca ggg cct gga ttt aca    1680
Leu Pro Asp Ser Pro Ser Pro Thr Ile Val Pro Gly Pro Gly Phe Thr
545                 550                 555                 560 ggg ggg gat ata ata caa tta ctg gcg aat aca aaa ggt ata gca aat    1728
Gly Gly Asp Ile Ile Gln Leu Leu Ala Asn Thr Lys Gly Ile Ala Asn
                565                 570                 575 atg aat ttt gaa att caa gac att aat aaa gaa tat att atg aga att    1776
Met Asn Phe Glu Ile Gln Asp Ile Asn Lys Glu Tyr Ile Met Arg Ile
            580                 585                 590 cgg tat gct tcc gct gca aat cct gaa ttc aat ata gct gtt ggt act    1824
Arg Tyr Ala Ser Ala Ala Asn Pro Glu Phe Asn Ile Ala Val Gly Thr
        595                 600                 605 agt gga gaa aga gtt agt act agt gct caa aaa act atg aat cca ggg    1872
Ser Gly Glu Arg Val Ser Thr Ser Ala Gln Lys Thr Met Asn Pro Gly
    610                 615                 620 gat att tta aca ttt aat aaa ttt aat tac gca act ttc cct ccc att    1920
Asp Ile Leu Thr Phe Asn Lys Phe Asn Tyr Ala Thr Phe Pro Pro Ile
625                 630                 635                 640 aaa ttt aat tca act aaa att tcg ata atg tta aca gca aga ttg gct    1968
Lys Phe Asn Ser Thr Lys Ile Ser Ile Met Leu Thr Ala Arg Leu Ala
                645                 650                 655 gct ttt gca agc aca tta ttg gaa acc tat ata gat aga atc gaa ttc    2016
Ala Phe Ala Ser Thr Leu Leu Glu Thr Tyr Ile Asp Arg Ile Glu Phe
            660                 665                 670 atc cca gta gat gaa aca tac gag gcg gag aca gat tta gaa acg gcg    2064
Ile Pro Val Asp Glu Thr Tyr Glu Ala Glu Thr Asp Leu Glu Thr Ala
        675                 680                 685 aag aaa gca gtg aat gcc ttg ttt acg aat aca aaa gat ggc tta cga    2112
Lys Lys Ala Val Asn Ala Leu Phe Thr Asn Thr Lys Asp Gly Leu Arg
    690                 695                 700 cca ggc gta acg gat tat gaa gtg aat caa gcg gca aac tta gtg tag    2160
Pro Gly Val Thr Asp Tyr Glu Val Asn Gln Ala Ala Asn Leu Val  *
705                 710                 715 ctcgag                                                             2166
```

<210> SEQ ID NO 2
<211> LENGTH: 719
<212> TYPE: PRT
<213> ORGANISM: Bacillus thuringiensis

<400> SEQUENCE: 2

```
Met Ser Pro Asn Asn Gln Asn Glu Tyr Glu Ile Ile Asp Ala Thr Pro
 1               5                  10                  15

Ser Thr Ser Val Ser Asn Asp Ser Asn Arg Tyr Pro Phe Ala Asn Glu
            20                  25                  30

Pro Thr Asn Ala Leu Gln Asn Met Asn Tyr Lys Asp Tyr Leu Arg Met
        35                  40                  45

Ser Glu Gly Tyr Asp Ser Glu Tyr Ser Gly Ser Pro Gly Ala Leu Val
    50                  55                  60
```

-continued

```
Ser Gly Lys Gln Ala Ile Lys Val Gly Ile Asp Ile Val Gly Asn Ile
 65                  70                  75                  80

Leu Gly Lys Leu Gly Val Pro Phe Ala Ser Gln Ile Val Ser Phe Tyr
                 85                  90                  95

Asn Phe Ile Leu Asp Gln Leu Trp Pro Ser Asn Ser Val Ser Val Trp
            100                 105                 110

Glu Gln Ile Met Thr Leu Val Glu Leu Val Asp Gln Lys Ile Thr
        115                 120                 125

Glu Tyr Ala Arg Asn Lys Ala Leu Ala Glu Leu Lys Gly Leu Gly Asp
    130                 135                 140

Ala Leu Gly Val Tyr Gln Gln Ser Leu Glu Ala Trp Leu Glu Asn Arg
145                 150                 155                 160

Asn Asp Thr Arg Ala Arg Ser Val Val Ser Asn Gln Phe Ile Ala Leu
                165                 170                 175

Glu Leu Asp Phe Val Gly Ala Ile Pro Ser Phe Ala Val Ser Gly Gln
            180                 185                 190

Glu Val Pro Leu Leu Ala Val Tyr Ala Gln Ala Val Asn Met His Leu
        195                 200                 205

Leu Leu Leu Arg Asp Ala Ser Ile Phe Gly Glu Glu Trp Gly Phe Thr
    210                 215                 220

Ser Ser Glu Ile Ser Thr Tyr Tyr Asn Arg Gln Val Gln Leu Thr Ser
225                 230                 235                 240

Gln Tyr Ser Asp Tyr Cys Val Lys Trp Tyr Asp Thr Gly Leu Gln Lys
                245                 250                 255

Leu Lys Gly Thr Ser Ala Glu Ser Trp Leu Glu Tyr His Gln Phe Arg
            260                 265                 270

Arg Glu Met Thr Phe Met Val Leu Asp Leu Val Ala Leu Phe Pro Asn
        275                 280                 285

Tyr Asp Thr His Thr Tyr Pro Leu Glu Thr Lys Ala Gln Leu Thr Arg
    290                 295                 300

Glu Val Tyr Thr Asp Pro Ile Ala Phe Asn Leu Ser Gly Ala Ala Gly
305                 310                 315                 320

Phe Cys Ser Pro Trp Ser Lys Tyr Thr Gly Ile Ser Phe Ser Glu Ile
                325                 330                 335

Glu Asn Asp Val Ile Arg Pro Pro His Leu Phe Asn Leu Leu Arg Ser
            340                 345                 350

Leu Glu Ile Asn Thr Val Arg Gly Thr Ile Leu Gly Asn Thr Lys Asp
        355                 360                 365

Tyr Leu Asn Tyr Trp Ser Gly His Ser Leu Gln Tyr Asn Phe Ile Gly
    370                 375                 380

Lys Thr Ile Val Arg Glu Ser Asn Tyr Gly Tyr Leu Thr Ser Glu Lys
385                 390                 395                 400

Thr Arg Ile Glu Leu Asp Thr Arg Asp Ile Phe Glu Ile Asn Ser Thr
                405                 410                 415

Ala Ala Ser Leu Ala Asn Tyr Tyr Gln Glu Thr Tyr Gly Val Pro Glu
            420                 425                 430

Ser Arg Leu His Leu Val Arg Trp Ala Ser Pro Tyr Tyr Thr Ser Ser
        435                 440                 445

His Leu Tyr Ser Lys Thr His Thr Thr Gly Glu Gly Cys Thr Gln Val
    450                 455                 460

Tyr Glu Ser Ser Glu Glu Ile Pro Val Asp Arg Thr Val Pro Ile Asn
465                 470                 475                 480
```

-continued

```
Glu Gly Tyr Ser His Arg Leu Ser Tyr Val Thr Ala Leu Phe Phe Gln
            485                 490                 495
Lys Ile Ile Asn Thr Phe Tyr Arg Asn Gly Thr Leu Pro Val Phe Val
            500                 505                 510
Trp Thr His Arg Ser Ala Asp Leu Thr Asn Thr Ile Tyr Pro Asp Val
            515                 520                 525
Ile Thr Gln Ile Pro Val Val Lys Ala Tyr Glu Leu Gly Ser Ser Ile
            530                 535                 540
Leu Pro Asp Ser Pro Ser Pro Thr Ile Val Pro Gly Pro Gly Phe Thr
545                 550                 555                 560
Gly Gly Asp Ile Ile Gln Leu Leu Ala Asn Thr Lys Gly Ile Ala Asn
            565                 570                 575
Met Asn Phe Glu Ile Gln Asp Ile Asn Lys Glu Tyr Ile Met Arg Ile
            580                 585                 590
Arg Tyr Ala Ser Ala Ala Asn Pro Glu Phe Asn Ile Ala Val Gly Thr
            595                 600                 605
Ser Gly Glu Arg Val Ser Thr Ser Ala Gln Lys Thr Met Asn Pro Gly
            610                 615                 620
Asp Ile Leu Thr Phe Asn Lys Phe Asn Tyr Ala Thr Phe Pro Pro Ile
625                 630                 635                 640
Lys Phe Asn Ser Thr Lys Ile Ser Ile Met Leu Thr Ala Arg Leu Ala
            645                 650                 655
Ala Phe Ala Ser Thr Leu Leu Glu Thr Tyr Ile Asp Arg Ile Glu Phe
            660                 665                 670
Ile Pro Val Asp Glu Thr Tyr Glu Ala Glu Thr Asp Leu Glu Thr Ala
            675                 680                 685
Lys Lys Ala Val Asn Ala Leu Phe Thr Asn Thr Lys Asp Gly Leu Arg
            690                 695                 700
Pro Gly Val Thr Asp Tyr Glu Val Asn Gln Ala Ala Asn Leu Val
705                 710                 715

<210> SEQ ID NO 3
<211> LENGTH: 28
<212> TYPE: DNA
<213> ORGANISM: Artificial Sequence
<220> FEATURE:
<223> OTHER INFORMATION: Cry8AB-75576 oligonucleotide primer

<400> SEQUENCE: 3
ggatccatga gtccaaataa tcaaaatg                                    28

<210> SEQ ID NO 4
<211> LENGTH: 26
<212> TYPE: DNA
<213> ORGANISM: Artificial Sequence
<220> FEATURE:
<223> OTHER INFORMATION: Cry8AB-73694 oligonucleotide primer

<400> SEQUENCE: 4
gcagtgaatg ccttgtttac gaatac                                      26
```

BACILLUS THURINGIENSIS CRY GENE AND PROTEIN

FIELD OF THE INVENTION

The present invention relates to the fields of plant molecular biology and plant pest control.

BACKGROUND OF THE INVENTION

Insect pests are a major factor in the loss of the world's agricultural crops. For example, corn rootworm feeding damage or boll weevil damage can be economically devastating to agricultural producers. Insect pest-related crop loss from corn rootworm alone has reached one billion dollars a year.

Traditionally, the primary methods for impacting insect pest populations, such as corn rootworm populations, are crop rotation and the application of broad-spectrum synthetic chemical pesticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative. Generally speaking, the use of biopesticides presents a lower risk of pollution and environmental hazards, and provides a greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* (Bt) and *Bacillus popilliae* are among the most successful biocontrol agents discovered to date. Insect pathogenicity has been attributed to strains of: *B. larvae, B. lentimorbus, B. popilliae, B. sphaericus*, Bt (Harwook, ed. (1989) *Bacillus* (Plenum Press), p. 306) and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial pesticides, particularly those obtained from *Bacillus* strains, have played an important role in agriculture as alternatives to chemical pest control. Pesticidal proteins isolated from strains of Bt, known as δ-endotoxins or Cry toxins, are initially produced in an inactive protoxin form. These protoxins are proteolytically converted into an active toxin through the action of proteases in the insect gut. See, Rukmini et al. (2000) *Biochimie* 82:109-116; Oppert (1999) *Arch. Insect Biochem. Phys.* 42:1-12; and Carroll et al. (1997) *J. Invertebrate Pathology* 70:41-49. Proteolytic activation of the toxin can include the removal of the N- and C-terminal peptides from the protein, as well as internal cleavage of the protein. Once activated, the Cry toxin binds with high affinity to receptors on epithelial cells in the insect gut, thereby creating leakage channels in the cell membrane, lysis of the insect gut, and subsequent insect death through starvation and septicemia. See, e.g., Li et al. (1991) *Nature* 353:815-821.

Recently, agricultural scientists have developed crop plants with enhanced insect resistance by genetically engineering crop plants with pesticidal genes to produce pesticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an environmentally friendly alternative to traditional insect-control methods. In addition, potatoes genetically engineered to contain pesticidal Cry toxins have been developed. These successes with genetic engineering have led researchers to search for novel pesticidal genes, particularly Cry genes. Therefore, novel homologues of known pesticidal genes are needed.

SUMMARY OF THE INVENTION

Compositions and methods for protecting a plant from a plant pest, particularly an insect pest, are provided. The compositions include novel nucleic acid molecules, and variants and fragments thereof, that encode pesticidal polypeptides. The amino acid sequences for the novel pesticidal polypeptides encoded by the nucleotide sequences of the embodiments are further provided. Compositions also include DNA constructs comprising a promoter operably linked to a nucleotide sequence that encodes a pesticidal polypeptide of the embodiments. Transformed plants, plant cells, seeds, and microorganisms comprising a polynucleotide of the embodiments are further provided.

The novel nucleic acid compositions of the embodiments find use in methods directed to protecting a plant from an insect pest. The methods comprise introducing into a plant a polynucleotide construct comprising a nucleotide sequence that encodes a pesticidal polypeptide of the embodiments operably linked to a promoter that drives expression in a plant. As a result, the pesticidal polypeptide is expressed in the plant and the insect pest is exposed to the protein at the site of insect attack. The presence of the pesticidal polypeptide protects the plant from the insect pest.

The embodiments further provide pesticidal compositions and formulations and methods for their use in controlling insect pests. Pesticidal compositions comprise a pesticidal polypeptide or transformed microorganism comprising a nucleotide sequence encoding a pesticidal polypeptide of the embodiments. Methods of using these compositions to impact an insect pest of a plant comprise applying the pesticidal composition to the environment of the insect pest.

DETAILED DESCRIPTION OF THE INVENTION

Methods and compositions directed to protecting a plant from an insect pest are provided. Compositions of the embodiments include novel nucleotide and amino acid sequences for pesticidal polypeptides. Specifically, the embodiments provide isolated nucleic acid molecules, and variants and fragments thereof, comprising the nucleotide sequence set forth in SEQ ID NO:1. Pesticidal polypeptides encoded by the novel nucleic acids of the embodiments are also provided. More particularly, compositions include pesticidal polypeptides having the amino acid sequence set forth in SEQ ID NO: 2, and variants and fragments thereof. Plants, plant cells, seeds, microorganisms, and DNA constructs comprising a nucleotide sequence of the embodiments that encodes a pesticidal polypeptide are also disclosed herein. Pesticidal compositions comprising an isolated pesticidal polypeptide of the embodiments, or a microorganism that expresses a nucleic acid of the embodiments, in combination with a carrier are further provided. The compositions of the embodiments find use in methods for protecting a plant from an insect pest or for impacting an insect pest.

The nucleic acid molecules of the embodiments comprise nucleotide sequences that are homologous to known pesticidal genes, particularly Bt Cry genes, more particularly Cry8A and Cry8B genes. The predicted amino acid sequence encoded by a nucleotide sequence of the embodiments is also disclosed as SEQ ID NO: 2. The present compositions can be used to practice the methods of the embodiments.

Methods directed to protecting a plant from a plant pest, particularly an insect pest, are provided. By "protecting a plant from an insect pest," limiting or eliminating insect pest-related damage to a plant by, for example, inhibiting the ability of the insect pest to grow, feed, and/or reproduce or by killing the insect pest is intended. The methods comprise introducing into a plant a polynucleotide construct comprising a nucleotide sequence that encodes a pesticidal polypeptide of the embodiments operably linked to a promoter that drives expression in a plant. As a result, the pesticidal polypeptide is expressed in the plant and the insect pest is exposed to the protein at the site of insect attack. The presence of the pesticidal polypeptide protects the plant from the insect pest.

While the embodiments do not depend on a particular biological mechanism for protecting a plant from an insect pest, expression of the nucleotide sequences of the embodiments in a plant can result in the production of active pesticidal polypeptides that increase the resistance of the plant to insect pests. The transgenic plants of the embodiments find use in agriculture in methods for protecting plants from insect pests and for impacting insect pests. Certain embodiments of the invention provide transformed crop plants, such as, for example, potato plants, which find use in methods for impacting the Colorado potato beetle.

In other embodiments, the pesticidal polypeptides encoded by the polynucleotides of the embodiments are disclosed as well as methods for using these polypeptides. Compositions and formulations comprising a pesticidal polypeptide, or variant or fragment thereof, are useful in methods for impacting an insect pest. "Impact an insect pest" or "impacting an insect pest" is intended to mean, for example, deterring the insect pest from feeding further on the plant, harming the insect pest, or killing the insect pest. In this manner, the embodiments further provide a method for impacting an insect pest of a plant comprising applying, for example, a composition or formulation comprising a pesticidal polypeptide to the environment of the insect pest. In one embodiment, the pesticidal polypeptide is combined with a carrier for subsequent application to the environment of the insect pest. While the embodiments are not bound by any theory of operation, in one embodiment, an insect pest ingests the pesticidal polypeptide, thereby impacting the insect pest.

One of skill in the art would recognize that the compositions and methods of the embodiments can be used alone or in combination with other compositions and methods for controlling insect pests that impact plants. For example, the embodiments may be used in conjunction with other pesticidal proteins or traditional chemical pesticides.

"Pesticidal gene" or "pesticidal polynucleotide" refers to a nucleotide sequence that encodes a polypeptide that exhibits pesticidal activity. As used herein, the term "pesticidal activity" refers to the ability of a substance, such as a polypeptide, to inhibit the growth, feeding, or reproduction of an insect pest and/or to kill the insect pest. A "pesticidal polypeptide," "pesticidal protein," or "insect toxin" is intended to mean a protein having pesticidal activity.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. In this manner, pesticidal activity impacts at least one measurable parameter of pest fitness. Assays for assessing pesticidal activity are well known in the art. See, e.g., U.S. Pat. Nos. 6,570,005 and 6,339,144.

The preferred developmental stage for testing for pesticidal activity is larvae or immature forms of these above-mentioned insect pests. The insects may be reared in total darkness at from about 20° C. to about 30° C. and from about 30% to about 70% relative humidity. Bioassays may be performed as described in Czapla and Lang (1990) *J. Econ. Entomol.* 83(6):2480-2485. Methods of rearing insect larvae and performing bioassays are well known to one of ordinary skill in the art.

A wide variety of bioassay techniques for assessing pesticidal activity is known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time.

In some embodiments of the invention, the pesticidal gene encodes a *Bacillus thuringiensis* (Bt) toxin, particularly a homologue of a known Cry toxin. "Bt" or "*Bacillus thuringiensis*" toxin is intended to mean the broader class of toxins found in various strains of Bt, which includes such toxins as, for example, the vegetative insecticidal proteins and the δ-endotoxins. See, for example, Crickmore et al. (1998) *Microbiol. Molec. Biol. Rev.* 62:807-813; and Crickmore et al. (2004) *Bacillus Thuringiensis Toxin Nomenclature* at lifesci.sussex.ac.uk/Home/Neil_Crickmore/Bt, both of which are herein incorporated by reference in their entirety. The vegetative insecticidal proteins (for example, members of the VIP1, VIP2, or VIP3 classes) are secreted insecticidal proteins that undergo proteolytic processing by midgut insect fluids. They have pesticidal activity against a broad spectrum of Lepidopteran insects. See, for example, U.S. Pat. No. 5,877,012, herein incorporated by reference in its entirety. The Bt δ-endotoxins are toxic to larvae of a number of insect pests, including members of the Lepidoptera, Diptera, and Coleoptera orders. These insect toxins include, but are not limited to, the Cry toxins, including, for example, Cry1, Cry3, Cry5, Cry8, and Cry9. Of particular interest are pesticidal genes that are homologous to known Cry8 genes.

The Bt toxins are a family of insecticidal proteins that are synthesized as protoxins and crystallize as parasporal inclusions. When ingested by an insect pest, the microcrystal structure is dissolved by the alkaline pH of the insect midgut, and the protoxin is cleaved by insect gut proteases to generate the active toxin. The activated Bt toxin binds to receptors in the gut epithelium of the insect, causing membrane lesions and associated swelling and lysis of the insect gut. Insect death results from starvation and septicemia. See, e.g., Li et al. (1991) *Nature* 353:815-821.

The protoxin form of the Cry toxins contains a crystalline forming segment. A comparison of the amino acid sequences of active Cry toxins of different specificities further reveals five highly-conserved sequence blocks. Structurally, the Cry toxins comprise three distinct domains, which are, from the N- to C-terminus: a cluster of seven alpha-helices implicated in pore formation (referred to as "domain 1"), three antiparallel beta sheets implicated in cell binding (referred to as "domain 2"), and a beta sandwich (referred to as "domain 3"). The location and properties of these domains are known to those of skill in the art. See, for example, Li et al. (1991) supra and Morse et al. (2001) *Structure* 9:409-417.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the term "polynucleotide" or "nucleotide" is not intended to limit the embodiments to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, but not limited to, single-stranded forms, double-stranded forms, hairpins, stem-and-loop structures, and the like.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

The embodiments encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the embodiments or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the embodiments. The term "fragment" is intended to mean a portion of the polynucleotide or a portion of the amino acid sequence and hence protein encoded thereby. Fragments of a polynucleotide may encode protein fragments that retain the biological activity of the native protein and hence have pesticidal activity. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotides encoding the proteins of the embodiments.

A fragment of a pesticidal polynucleotide that encodes a biologically active portion of a pesticidal protein of the embodiments will encode at least 15, 25, 30, 50, 100, 150, 200, 250, 300, 350, 400, 450, 500, 550, 600, or 650 contiguous amino acids, or up to the total number of amino acids present in a full-length pesticidal protein of the embodiments (for example, 719 amino acids for SEQ ID NO:2). Fragments of a pesticidal polynucleotide that are useful as hybridization probes or PCR primers generally need not encode a biologically active portion of a pesticidal protein.

Thus, a fragment of a pesticidal polynucleotide may encode a biologically active portion of a pesticidal polypeptide, or it may be a fragment that can be used as a hybridization probe or PCR primer using methods disclosed below. A biologically active portion of a pesticidal polypeptide can be prepared by isolating a portion of one of the pesticidal polynucleotides of the embodiments, expressing the encoded portion of the pesticidal protein (e.g., by recombinant expression in vitro), and assessing the activity of the encoded portion of the pesticidal protein. Polynucleotides that are fragments of a pesticidal gene comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,450, 1,500, 1,550, 1,600, 1,650, 1,700, 1,750, 1,800, 1,850, 1,900, 1,950, or 2,000 contiguous nucleotides, or up to the number of nucleotides present in a full-length pesticidal polynucleotide disclosed herein (for example, 2166 nucleotides for SEQ ID NO:1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the pesticidal polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a pesticidal protein of the embodiments. Generally, variants of a particular polynucleotide of the embodiments will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2 is disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, pesticidal activity as described herein. Such variants may result from, for example, genetic polymorphism or from human manipulation. Biologically active variants of a native pesticidal polypeptide of the embodiments will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the embodiments may differ from that protein by as few as 1-15 amino acid residues, as few as 1-10, such as 6-10, as few as 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the pesticidal proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal Thus, the genes and polynucleotides of the embodiments include both the naturally occurring sequences as well as mutant forms. Likewise, the proteins of the embodiments encompass both naturally occurring proteins as well as variations and modified forms thereof. Such variants will continue to possess the desired pesticidal activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity of a pesticidal polypeptide can be evaluated by, for example, insect-feeding assays. See, e.g., Marrone et al. (1985) *J. Econ. Entomol.* 78:290-293 and Czapla and Lang (1990) supra, herein incorporated by reference.

Variant polynucleotides and proteins also encompass sequences and proteins derived from a mutagenic and recombinogenic procedure such as DNA shuffling. With such a procedure, one or more different pesticidal polypeptide coding sequences can be manipulated to create a new pesticidal polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the pesticidal gene of the embodiments and other known pesticidal genes to obtain a new gene coding for a protein with an improved property of interest, such as an increased pesticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:450-44509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other microorganisms. In this manner, methods such as PCR, hybridization, and the like can be used to identify such sequences based on their sequence homology to the sequences set forth herein. Sequences isolated based on their sequence identity to the entire pesticidal sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for a pesticidal polypeptide and which hybridize under stringent conditions to the pesticidal sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the pesticidal polynucleotides of the embodiments. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire pesticidal polynucleotide disclosed herein, or one or more portions thereof, may be used as a probe capable of specifically hybridizing to corresponding pesticidal polynucleotide and messenger RNAs. To achieve specific hybridization under a variety of conditions, such probes include sequences that are unique among pesticidal polynucleotide sequences and are optimally at least about 10 nucleotides in length, and most optimally at least about 20 nucleotides in length. Such probes may be used to amplify corresponding pesticidal polynucleotide from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N. Y.); and Ausubel et al., eds. (1995) *Current Protocols in Molecular Biology*, Chapter 2 (Greene Publishing and Wiley-Interscience, New York). See Sambrook et al. (1989) supra.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The pesticidal polynucleotides of the embodiments can be provided in DNA constructs (or expression cassettes) for expression in the plant or microorganism of interest. The construct will include 5' and 3' regulatory sequences operably linked to a pesticidal polynucleotide of the embodiments. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The construct may additionally contain at least one additional gene to be cotransformed into the organism. Alternatively, the additional gene(s) can be provided on multiple DNA constructs. Such a DNA construct is provided with a plurality of restriction sites and/or recombination sites for insertion of a polynucleotide of the embodiments to be under the transcriptional regulation of the regulatory regions. The DNA construct may additionally contain selectable marker genes.

The DNA construct will include in the 5'-3' direction of transcription, a transcriptional initiation region, translational initiation region, a heterologous nucleotide sequence of interest (i.e. a sequence of the embodiments), a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The DNA constructs may additionally contain 5' leader sequences. Such leader sequences can act to enhance translation. Translation leaders are known in the art and include: picornavirus leaders, for example, EMCV leader (Encephalomyocarditis 5' noncoding region)(Elroy-Stein et al. (1989) *Proc. Natl. Acad. Sci. USA* 86:6126-6130); potyvirus leaders, for example, TEV leader (Tobacco Etch Virus)(Gallie et al. (1995) *Gene* 165(2):233-238), MDMV leader (Maize Dwarf Mosaic Virus), and human immunoglobulin heavy-chain binding protein (BiP)(Macejak et al. (1991) *Nature* 353:90-94); untranslated leader from the coat protein mRNA of alfalfa mosaic virus (AMV RNA 4)(Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV)(Lommel et al. (1991) *Virology* 81:382-385). See also, Della-Cioppa et al. (1987) *Plant Physiol.* 84:965-968.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The DNA construct can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP)(Su et al. (2004) *Biotechnol. Bioeng.* 85:610-9 and Fetter et al. (2004) Plant Cell 16:215-28), cyan fluorescent protein (CYP)(Bolte et al. (2004) *J. Cell Science* 117:943-54 and Kato et al. (2002) *Plant Physiol.* 129:913-42), and yellow fluorescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the embodiments.

A number of promoters can be used in the practice of the embodiments, including the native promoter of the polynucleotide sequence of interest. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol Biol.* 18:675-689); pEMU (Last et al. (1991) *Theor. Appl. Genet* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al., (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol Mol. Plant Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue, particularly within a tissue that is likely to be the target of pest attack. In particular embodiments, a pesticidal polypeptide is selectively expressed in tissues where insect-related damage is likely to occur. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus comiculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. Other root-preferred promoters of interest are disclosed in U.S. patent application Ser. No. 11/022,111, entitled "Maize Metallothionein Promoter," filed Dec. 22, 2004, and U.S. patent application Ser. No. 11/022,449, entitled "Maize Metallothionein 2 Promoter and Methods of Use," filed Dec. 22, 2004, both of which are herein incorporated by reference in their entirety.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); mi1ps (myo-inositol-1-phosphate synthase)(see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al., (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the nucleotide sequences of the embodiments can be provided to a plant using a variety of transient transformation methods. Such transient transformation methods include, but are not limited to, the introduction of the pesticidal protein or variants and fragments thereof directly into the plant or the introduction of the pesticidal polypeptide transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci. USA* 91:2176-2180 and Hush et al. (1994) *J. Cell Science* 107:775-784, all of which are herein incorporated by reference. Alternatively, the pesticidal polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethyleneimine (PEI; Sigma #P3143).

In other embodiments, the polynucleotide of the embodiments may be introduced into plants by contacting plants with a virus or viral nucleic acids. Generally, such methods involve incorporating a nucleotide construct of the embodiments within a viral DNA or RNA molecule. It is recognized that the a pesticidal polypeptide of the embodiments may be initially synthesized as part of a viral polyprotein, which later may be processed by proteolysis in vivo or in vitro to produce the desired recombinant protein. Further, it is recognized that promoters of the embodiments also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853, all of which are herein incorporated by reference. Briefly, the polynucleotide of the embodiments can be contained in a transfer cassette flanked by two non-recombinogenic recombination sites. The transfer cassette is introduced into a plant having stably incorporated into its genome a target site that is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provide transformed seed (also referred to as "transgenic seed") having a polynucleotide of the embodiments, for example, a DNA construct of the embodiments, stably incorporated into their genome.

Pedigree breeding starts with the crossing of two genotypes, such as an elite line of interest and one other elite inbred line having one or more desirable characteristics (i.e., having stably incorporated a polynucleotide of the embodiments, having a modulated activity and/or level of the polypeptide of the embodiments, etc.) that complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of a maize inbred line of interest, comprising the steps of crossing a plant of the maize inbred line of interest with a donor plant comprising a mutant gene or transgene conferring a desired trait (i.e., resistance to insect pests), selecting an F1 progeny plant comprising the mutant gene or transgene conferring the desired trait, and backcrossing the selected F1 progeny plant to the plant of the maize inbred line of interest. This method may further comprise the step of obtaining a molecular marker profile of the maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of the maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross-pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Instead of self-pollination, directed-pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "*Principals of Cultivar Development*" Fehr (1993)(Macmillan Publishing Company), the disclosure of which is incorporated herein by reference. In addition, mutations created in other lines may be used to produce a backcross conversion of elite lines that comprises such mutations.

In certain embodiments the polynucleotides of the embodiments can be stacked with any combination of polynucleotide sequences of interest in order to create plants with a desired trait. A trait, as used herein, refers to the phenotype derived from a particular sequence or groups of sequences. For example, the polynucleotides of the embodiments may be stacked with any other polynucleotides encoding polypeptides having pesticidal and/or insecticidal activity, such as other Bt toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981, 722), and the like. The combinations generated can also include multiple copies of any one of the polynucleotides of interest. The polynucleotides of the embodiments can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)); the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262: 1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 99/25821, WO 99/25854, WO 99/25840, WO 99/25855, and WO 99/25853, all of which are herein incorporated by reference.

As used herein, the term plant includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The sequences of the embodiments may be used for transformation and protection of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants included are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mung bean, lima bean, fava bean, lentils, chickpea, etc.

Pesticidal compositions are also encompassed by the embodiments. Pesticidal compositions may comprise pesticidal polypeptides or microorganisms comprising a nucleotide sequence that encodes a pesticidal polypeptide. The pesticidal compositions of the embodiments may be applied to the environment of a plant pest, as described herein below, thereby protecting a plant from a plant pest. Moreover, a pesticidal composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

A gene encoding a pesticidal polypeptide of the embodiments, particularly a Bt Cry toxin, may be introduced into any suitable microbial host according to standard methods in the art. For example, microorganism hosts that are known to occupy the "phytosphere" (phylloplane, phyllosphere, rhizosphere, and/or rhizoplane) of one or more crops of interest may be selected. These microorganisms are selected so as to be capable of successfully competing in the particular environment with the wild-type microorganisms, and to provide for stable maintenance and expression of the gene expressing the pesticidal protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthro-* bacter, *Azotobacter, Leuconostoc,* and *Alcaligenes,* fungi, particularly yeast, e.g., *Saccharomyces, Cryptococcus, Kluyveromyces, Sporobolomyces, Rhodotorula,* and *Aureobasidium.* Of particular interest are such phytosphere bacterial species as *Pseudomonas syringae, Pseudomonas fluorescens, Serratia marcescens, Acetobacterxylinum, Agrobacteria, Rhodopseudomonas spheroides, Xanthomonas campestris, Rhizobium melioti, Alcaligenes entrophus, Clavibacter xyli* and *Azotobacter vinlandii,* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

Other illustrative prokaryotes, both Gram-negative and gram-positive, include Enterobacteriaceae, such as *Escherichia, Erwinia, Shigella, Salmonella,* and *Proteus*; Bacillaceae; Rhizobiaceae, such as *Rhizobium*; Spirillaceae, such as photobacterium, *Zymomonas, Serratia, Aeromonas, Vibrio, Desulfovibrio,* and *Spirillum*; Lactobacillaceae; Pseudomonadaceae, such as *Pseudomonas* and *Acetobacter*; Azotobacteraceae; and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces,* and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae,* Bt, *Escherichia coli, Bacillus subtilis,* and the like.

Genes encoding the pesticidal polypeptides of the embodiments can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal polypeptides of the embodiments can be introduced into a root-colonizing *Bacillus cereus* by standard methods known in the art.

Genes encoding pesticidal proteins can be introduced, for example, into the root-colonizing *Bacillus* by means of electrotransformation. Specifically, genes encoding the pesticidal proteins can be cloned into a shuttle vector, for example, pHT3101 (Lerecius et al. (1989) *FEMS Microbiol. Letts.* 60:211-218. The shuttle vector pHT3101 containing the coding sequence for the particular pesticidal gene can, for example, be transformed into the root-colonizing *Bacillus* by means of electroporation (Lerecius et al. (1989) *FEMS Microbiol. Letts.* 60:211-218).

Methods are provided for protecting a plant from a plant pest comprising applying an effective amount of a pesticidal protein or composition of the embodiments to the environment of the pest. By "effective amount" is intended an amount of a protein or composition sufficient to control a plant pest. The pesticidal proteins and compositions can be applied to the environment of the pest by methods known to those of ordinary skill in the art.

The pesticidal compositions of the embodiments may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the pesticidal proteins, more particularly Cry toxins, of the embodiments include, but are not limited to, foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The pesticidal compositions of the embodiments can be in a suitable form for direct application or as a concentrate of a primary composition that requires dilution with a suitable quantity of water or other diluent before application. The concentration of the pesticidal polypeptide will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb.-5.0 lb. per acre when in dry form and at about 0.01 pts.-10 pts. per acre when in liquid form.

In a further embodiment, the compositions, as well as the transformed microorganisms and pesticidal proteins, of the embodiments can be treated prior to formulation to prolong the pesticidal activity when applied to the environment of a target pest as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The pesticidal compositions of the embodiments can be applied to the environment of a plant pest by, for example, spraying, atomizing, dusting, scattering, coating or pouring, introducing into or on the soil, introducing into irrigation water, by seed treatment or general application or dusting at the time when the pest has begun to appear or before the appearance of pest as a protective measure. For example, the pesticidal protein and/or transformed microorganisms of the embodiments may be mixed with grain to protect the grain during storage. It is generally important to obtain good control of pest in the early stages of plant growth, as this is the time when the plant can be most severely damaged. The compositions of the embodiments can conveniently contain an insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, a herbicide, an insecticide, a fertilizer, an inert carrier, and dead cells of a *Bacillus* strain or transformed microorganism of the embodiments.

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protective coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protective coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a DNA molecule comprising a nucleotide sequence encoding a pesticidal polypeptide of the embodiments may be treated with a seed protective coating comprising a seed treatment compound, such as, for example, captan, carboxin, thiram, methalaxyl, pirimiphos-methyl, and others that are commonly used in seed treatment. Alternatively, a seed of the embodiments comprises a seed protective coating comprising a pesticidal composition of the embodiments is used alone or in combination with one of the seed protective coatings customarily used in seed treatment.

The methods and compositions of the embodiments may be effective against a variety of pests. For purposes of the embodiments, pests include, but are not limited to, insects, fungi, bacteria, nematodes, acarids, protozoan pathogens, animal-parasitic liver flukes, and the like. Pests of particular interest are insect pests, particularly insect pests that cause significant damage to agricultural plants.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. These include larvae of the order Lepidoptera, such as armyworms, cutworms, loopers, and heliothines in the family Noctuidae (e.g., fall armyworm (*Spodoptera frugiperda* J. E. Smith), beet armyworm (*Spodoptera exigua* Hübner), bertha armyworm (*Mamestra configurata* Walker), black cutworm (*Agrotis ipsilon* Hufnagel), cabbage looper (*Trichoplusia ni* Hübner), soybean looper (*Pseudoplusia includens* Walker), velvetbean caterpillar (*Anticarsia gemmatalis* Hübner), green cloverworm (*Hypena scabra* Fabricius) tobacco budworm (*Heliothis virescens* Fabricius), granulate cutworm (*Agrotis subterranea* Fabricius), armyworm (*Pseudaletia unipuncta* Haworth) western cutworm (*Agrotis orthogonia* Morrison)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker), sunflower moth (*Homoeosoma electellum* Hulst), lesser cornstalk borer (*Elasmopalpus lignosellus* Zeller)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), sunflower bud moth (*Suleima helianthana* Riley)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus), clover leaf weevil (*Hypera punctata* Fabricius), maize billbug (*Sphenophorus maidis* Chittenden)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte), northern corn rootworm (*Diabrotica barberi* Smith & Lawrence); southern corn rootworm (*Diabrotica undecimpunctata howardi* Barber), corn flea beetle (*Chaetocnema pulicaria* Melsheimer), crucifer flea beetle (*Phyllotreta cruciferae* Goeze), grape colaspis (*Colaspis brunnea* Fabricius), cereal leaf beetle (*Oulema melanopus* Linnaeus), sunflower beetle (*Zygogramma exclamationis* Fabricius)); beetles from the family Coccinellidae (e.g. Mexican bean beetle (*Epilachna varivestis* Mulsant); chafers and other beetles from the family Scarabaeidae (e.g., Japanese beetle (*Popillia japonica* Newman), northern masked chafer (white grub) (*Cyclocephala borealis* Arrow), southern masked chafer (white grub)(*Cyclocephala immaculate* Olivier), European chafer (*Rhizotrogus majalis* Razoumowsky), white grub (*Phyllophaga crinita* Burmeister), carrot beetle (*Ligyrus gibbosus* De Geer)); carpet beetles from the family Dermestidae; wireworms from the family Elateridae (e.g., *Melanotus* spp., *Conoderus* spp., *Limonius* spp., *Agriotes* spp., *Ctenicera* spp., *Aeolus* spp.); bark beetles from the family Scolytidae and beetles from the family Tenebrionidae (e.g. *Eleodes* spp). In addition it includes: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidea and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae.

Also included are adults and larvae of the order Acari (mites) such as wheat curl mite (*Aceria tosichella* Keifer), brown wheat mite (*Petrobia latens* Müller), spider mites and red mites in the family Tetranychidae (e.g., European red mite (*Panonychus ulmi* Koch), two spotted spider mite (*Tetranychus urticae* Koch), McDaniel mite (*T. mcdanieli* McGregor), carmine spider mite (*T. cinnabarinus* Boisduval), strawberry spider mite (*T. turkestani* Ugarov & Nikolski)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius (migratory grasshopper), *M. differentialis* Thomas (differential grasshopper), *M. femurrubrum* De Geer, (redlegged grasshopper)), American grasshoppers (e.g., *Schistocerca americana* Drury), desert locust (*S. gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers (e.g. *Agromyza parvicomis* Loew (corn blotch leafminer)), midges (e.g., *Contarinia sorghicola* Coquilleft (sorghum midge), *Mayetiola destructor* Say (Hessian fly), *Sitodiplosis mosellana* Géhin, (wheat midge), *Neolasioptera murtfeldtiana* Felt, (sunflower seed midge)), fruit flies (Tephritidae), frit flies (e.g., *Oscinella frit* Linnaeus), maggots (e.g., *Delia platura* Meigen (seedcorn maggot) and other *Delia* spp., *Meromyza americana* Fitch (wheat stem maggot)), house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman), grass thrips (*Anaphothrips obscrurus* Müller), tobacco thrips (*Frankliniella fusca* Hinds), western flower thrips (*Frankliniella occidentalis* Pergande), soybean thrips (*Neohydatothrips variabilis* Beach), citrus thrips (*Scirthothrips citri* Moulton) and other foliar feeding thrips; insect pests of the order Hymenoptera including sawflies (e.g. wheat stem sawfly (*Cephus cinctus* Norton)), ants (e.g., red carpenter ant (*Camponotus ferrugineus* Fabricius), black carpenter ant (*C. pennsylvanicus* De Geer), Pharaoh ant (*Monomorium pharaonis* Linnaeus), little fire ant (*Wasmannia auropunctata* Roger), fire ant (*Solenopsis geminata* Fabricius), thief ant (*Solenopsis molesta* Say), red imported fire ant (*S. invicta* Buren), Argentine ant (*Iridomyrmex humilis* Mayr), crazy ant (*Paratrechina longicomis* Latreille), pavement ant (*Tetramorium caespitum* Linnaeus), cornfield ant (*Lasius alienus* Forster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*R. hesperus* Banks), Formosan subterranean termite (*Coptotemes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*P. humanus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurystemus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*C. canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Compounds of the embodiments may show high activity against agronomic pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrocis medinalis* Guenée (rice leaf roller), *Crambus caliginosellus* Clemens (corn root webworm), *C. teteffellus* Zincken (bluegrass webworm), *Diatraea grandiosella* Dyar (southwestern corn borer), *D. saccharalis* Fabricius (surgarcane borer), *Earias insulana* Boisduval (spiny bollworm), *E. viffella* Fabricius (spotted bollworm), *Helicoverpa armigera* Hübner (American bollworm), *H. zea* Boddie (corn earworm or cotton bollworm), *Heliothis virescens* Fabricius (tobacco budworm), *Herpetogramma licarsisalis* Walker (sod webworm), *Lobesia botrana* Denis & Schiffermüller (European grape vine moth), *Pectinophora gossypiella* Saunders (pink bollworm), *Phyllocnistis citrella* Stainton (citrus leafminer), *Pieris brassicae* Linnaeus (large white butterfly), *P. rapae* Linnaeus (small white butterfly), *Plutella xylostella* Linnaeus (diamondback moth), *Spodoptera exigua* Hübner (beet armyworm), *S. litura* Fabricius (tobacco cutworm, cluster caterpillar), *S. frugiperda* J. E. Smith (fall armyworm), and *Tuta absoluta* Meyrick (tomato leafminer)).

Compounds of the embodiments may also have commercially significant activity on agronomically important members from the order Homoptera including: *Acyrthisiphon pisum* Harris (pea aphid), *Aphis craccivora* Koch (cowpea aphid), *A. fabae* Scopoli (black bean aphid), *A. gossypii* Glover (cotton aphid, melon aphid), *A. maidiradicis* Forbes (corn root aphid), *A. pomi* De Geer (apple aphid), *A. spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Brevicoryne brassicae* Linnaeus (cabbage aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *R. padi* Linnaeus (bird cherry-oat aphid), *Schizaphis graminum* Rondani (greenbug), *Sipha flava* Forbes, (yellow sugarcane aphid), *Sitobion avenae* Fabricius (English grain aphid), *Therioaphis maculata* Buckton (spotted alfalfa aphid), *Toxoptera aurantii* Boyer de Fonscolombe (black citrus aphid), and *T. citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *B. argentifolii* Bellows & Perring (silverleaf whitefly), *Dialeurodes citri* Ashmead (citrus whitefly), *Trialeurodes abutiloneus* (bandedwinged whitefly) and *T. vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *N. nigropictus* Stål (rice leafhopper), *Nilaparvata lugens* Stål (brown planthopper), *Peregrinus maidis* Ashmead (corn planthopper), *Sogatella furcifera* Horvath (whitebacked planthopper), *Sogatodes orizicola* Muir (rice delphacid), *Typhlocyba pomaria* McAtee white apple leafhopper, *Erythroneoura* spp. (grape leafhoppers); *Magicicada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of the embodiments may also have activity on members from the order Hemiptera including: *Acrostemum hilare* Say (green stink bug), *Anasa tristis* De Geer (squash bug), *Blissus leucoptenis leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euschistus servus* Say (brown stink bug), *Euschistus variolarius* Palisot de Beauvois (one-spotted stink bug), *Graptostethus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper).

The article "a" and "an" are used herein to refer to one or more than one (i.e., to at least one) of the grammatical object of the article. By way of example, "an element" means one or more element.

The following examples are provided by way of illustration, not by way of limitation.

EXPERIMENTAL

Example 1

Identification of Novel Cry8A/Cry8B Homologues from Bt

A potentially novel Cry8A/Cry8B homologue was identified from Dupont Bt strains. A series of sequence analyses steps was then performed to determine if the identified homologue was novel.

Sequencing Characterization of Potentially Novel Cry8A/Cry8B Homologue

Cloning of 88 kD Fragment of Cry8A/Cry8B Gene

PCR primers were designed for cloning an 88 kD fragment (including the toxin domain) from the N-terminus of the potentially novel Cry8A/Cry8B gene. The following PCR primers were used:

```
                                              (SEQ ID NO: 3)
Cry8AB-75576:  GGATCCATGAGTCCAAATAATCAAAATG (SEQ ID NO: 4)
Cry8AB-73694:  GCAGTGAATGCCTTGTTTACGAATAC
```

The PCR products were cloned into a TA vector. Constructs containing the potentially novel Cry8A/Cry8B gene were then sequenced again.

Primary Sequence Analysis of Potential Novel Cry8A/Cry8B Gene

To assess the novelty of the selected sequence, the nucleic acid sequence data from the N-terminus and C-terminus (approximately 650 bp from each terminus) of the toxin domain for the potentially novel Cry8A/Cry8B homologue was analyzed using BLAST searches against known pesticidal genes from public Bt databases and published patents. The entire 88 kD fragment for the potentially novel sequence was sequenced and cloned into an expression vector. Table 1 shows the percent identity of the toxin domain of the novel Cry8A/Cry8B gene and known Cry8 genes.

TABLE 1

Percent Identity of the Novel Cry8AB Homologue Toxin Domain

|  | Cry8Aa | Cry8Ba | Cry8Bb | Cry8Bc | Cry8Ca | Cry8Da |
|---|---|---|---|---|---|---|
| Cry8AB008.1 (SEQ ID NO: 1) | 73.4 | 62.6 | 63.8 | 66.7 | 57.1 | 67.1 |

Secondary Sequence Analysis of Potential Novel Cry8A/Cry8B Gene

The sequence data for the entire 88 kD fragment of the potentially novel Cry8A/Cry8B homologue was analyzed using BLAST searches against known pesticidal genes from public Bt databases and published patents. The percent identity of the 88 kD fragment relative to known pesticidal genes was used to further assess the novelty of the selected sequence.

Final Sequence Analysis of Potentially Novel Cry8A/Cry8B Gene

Once the sequence was determined to be novel by the secondary sequence analysis, further analysis was performed by Southern blot and dot blot. Gene libraries for those Bt strains that harbor potential novel Cry8A/Cry8B genes were generated, and the full-length sequence for the potentially novel gene was determined. Genome-walking experiments were performed to confirm the novelty of the identified sequence.

Expression of Novel Cry8A/Cry8B Gene and Bioassays for Pesticidal Activity

The DNA fragment representing 88 kDa for the novel Cry8A/Cry8B gene was cloned into pET20b expression vectors (Clontech). The His-Tag polypeptides encoded by the novel genes were purified using Talon Metal Affinity Resin (BD Bioscience Clontech) and used in bioassays for assessing pesticidal activity against western corn rootworm (WCRW), Colorado potato beetle (CPB), and southern corn rootworm (SCRW). Such bioassays are well known in the art. See, for example, Czapla and Lang (1990) *J. Econ. Entomol.* 83(6):2480-2485 and U.S. Pat. Nos. 6,570,005 and 6,339,144. The results of the bioassay are summarized below in Table 2.

TABLE 2

Pesticidal Activity of Novel Cry8A/Cry8B Toxins

|  | Toxin Domain | Expression | Pesticidal Activity |
|---|---|---|---|
| Cry8AB008.1 (SEQ ID NO: 1) | Full | Yes | CPB active |

Example 2

Transformation and Regeneration of Transgenic Plants

Immature maize embryos from greenhouse donor plants are bombarded with a plasmid containing the novel Cry8A/Cry8B gene designated Cry8AB001.1 (SEQ ID NO:1) operably linked to the ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the Cry8AB001.1 (SEQ ID NO:1) operably linked to the ubiquitin promoter is made. This plasmid DNA plus plasmid DNA containing a PAT selectable marker is precipitated onto 1.1 µm (average diameter) tungsten pellets using a $CaCl_2$ precipitation procedure as follows: 100 µL prepared tungsten particles in water; 10 µL (1 µg) DNA in Tris EDTA buffer (1 µg total DNA); 100 µL 2.5 M $CaCl_2$; and 10 µL 0.1 M spermidine.

Each reagent is added sequentially to the tungsten particle suspension, while maintained on the multi-tube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 µL 100% ethanol is added to the final tungsten particle pellet. For particle gun bombardment, the tungsten/DNA particles are briefly sonicated and 10 µL spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of Cry8AB001.1 by assays known in the art, such as, for example, immunoassays and western blotting.

Analysis of Transgenic Maize Plants

Transgenic maize plants positive for expression of Cry8AB001.1 are tested for resistance to WCRW, CPB, and SCRW using standard bioassays known in the art. Such methods include, for example, root excision bioassays and whole plant bioassays. See, e.g., U.S. Patent Publication No. US 2003/0120054 and International Publication No. WO 03/018810.

Bombardment medium (560Y) comprises 4.0 g/L N6 basal salts (SIGMA C-1416), 1.0 mL/L Eriksson's Vitamin Mix (1000×SIGMA-1511), 0.5 mg/L thiamine HCl, 120.0 g/L sucrose, 1.0 mg/L 2,4-D, and 2.88 g/L L-proline (brought to volume with D-1 $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$)(Murashige and Skoog (1962) *Physiol. Plant* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 3

*Agrobacterium*-Mediated Transformation of Maize

For *Agrobacterium*-mediated transformation of maize with the Cry8AB001.1 nucleotide sequence (SEQ ID NO:1), the method of Zhao is employed (U.S. Pat. No. 5,981,840, and International Patent Publication No. WO 98/32326; the contents of which are hereby incorporated by reference). Briefly, immature embryos are isolated from maize and the embryos contacted with a suspension of *Agrobacterium*, where the bacteria are capable of transferring the Cry8AB001.1 gene to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 4

Soybean Embryo Transformation

Soybean embryos are bombarded with a plasmid containing the novel Cry8A/Cry8B gene designated Cry8AB001.1 (SEQ ID NO:1) operably linked to a ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (*London*) 327:70-73, U.S. Pat. No. 4,945,050). A Dupont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the Cry8AB001.1 (SEQ ID NO:1) operably linked to the ubiquitin promoter can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications and patent applications mentioned in the specification are indicative of the level of those skilled in the art to which the embodiments of this invention pertain. All publications and patent applications are herein incorporated by reference to the same extent as if each individual publication or patent application was specifically and individually indicated to be incorporated by reference.

Although the foregoing embodiments have been described in some detail by way of illustration and example for purposes of clarity of understanding, it will be obvious that certain changes and modifications may be practiced within the scope of the appended claims.

That which is claimed:

1. An isolated polypeptide comprising an amino acid sequence selected from the group consisting of:
   a) the amino acid sequence set forth in SEQ ID NO:2;
   b) an amino acid sequence having at least 95% sequence identity to SEQ ID NO:2, wherein said polypeptide has pesticidal activity;
   c) the amino acid sequence encoded by the nucleotide sequence of SEQ ID NO:1; and,
   d) an amino acid sequence comprising at least 600 consecutive amino acids of SEQ ID NO:2, wherein said polypeptide has pesticidal activity.

* * * * *